United States Patent [19]

Holly, deceased et al.

[11] 4,439,359

[45] Mar. 27, 1984

[54] CYCLIC OCTAPEPTIDE ANALOGS OF NEUROTENSIN

[75] Inventors: Frederick W. Holly, deceased, late of Glenside, Pa., by Evelyn H. Holly, executrix; Marcia E. Christy, Perkasie, Pa.; Kenneth L. Shepard, West Point, Pa.; Robert G. Strachan, Warrington, Pa.; Sandor L. Varga, Harleysville, Pa.; Daniel F. Veber, Ambler, Pa.

[73] Assignee: Merck & Co., Inc., Rahway, N.J.

[21] Appl. No.: 394,750

[22] Filed: Jul. 2, 1982

[51] Int. Cl.³ .......................................... C07C 103/52
[52] U.S. Cl. .............................................. 260/112.5 R
[58] Field of Search ................................. 260/112.5 R

[56] References Cited

PUBLICATIONS

J. Med. Chem., 24, 370–376 (1981), St. Pierre, et al.
J. Biol. Chem., 251, 7035–7044 (1976), R. Carraway, et al.
Mol. Pharm., 18, 11–19 (1980), P. Kitabgi, et al.
J. Med. Chem., 20, No. 11, 1409–1412 (1977), J. E. Rivier, et al.

*Primary Examiner*—Delbert R. Phillips
*Attorney, Agent, or Firm*—Salvatore C. Mitri

[57] ABSTRACT

There are disclosed cyclic octapeptide analogs of the tridecapeptide, neurotensin.

6 Claims, No Drawings

CYCLIC OCTAPEPTIDE ANALOGS OF NEUROTENSIN

BACKGROUND OF THE INVENTION

The tridecapeptide, neurotensin (NT) is known to have a wide variety of pharmacological effects, including those common to peptides in the kinin group. NT is also known to have activity within the central nervous system producing hypothermia, a reduction in locomotor activity and an antinocispusive effect in rodents. These pharmacological actions of NT suggest that the peptide is a neurotransmitter or neuromodulator. Consequently, this tridecapeptide holds a great deal of potential for a host of therapeutic applications.

A solid-phase method for preparing peptides, including NT, and analogs of NT modified at the C-terminal end of the molecule is described by St. Pierre, et al. [J. Med. Chem., 24, 370–376 (1981)].

The structural requirements for biological activity of NT and methods for obtaining partial sequences of this tridecapeptide have been reported by R. Carraway, et al., [J. Biol. Chem., 251, 7035–7044 (1976)].

The binding affinity of NT and NT analogs has been examined by P. Kitabgi, et al., [Mol. Pharm., 18, 11–19 (1980)] and the activity relationships of a series of NT analogs and their relative potencies has been explored by J. E. Rivier, et al. [J. Med. Chem., 20, No. 11, 1409–1412 (1977)]. J. E. Rivier, et al., also disclose cyclic NT analogs wherein the entire tridecapeptide is cyclized.

There are no known cyclic peptides smaller than cyclized NT that exhibit NT-like activity.

SUMMARY OF THE INVENTION

It has been surprisingly found that cyclic octapeptide analogs of NT exhibit NT-like activity. These cyclic octapeptide analogs can be represented by the general formula:

Cyclo(D-Lys-Pro-B-B-Pro-C-Ile-Leu)    (I)

wherein:
B is a basic amino acid residue (such as 2,4-diaminobutyric acid, lysine, arginine, ornithine, homoarginine, and the like); and
C is tyrosine or tryptophane.

Preferred cyclic compounds of Formula I are those wherein:
B is lysine or ornithine; and,
C is tyrosine or tryptophane.

Most preferred cyclic compounds of Formula I are those wherein:
B is lysine; and,
C is tyrosine.

Processes by which the cyclic octapeptide analogs of the invention can be obtained are illustrated in the following Reaction Schemes wherein R denotes a resin such as a chloromethylated polystyrene-divinylbenzene copolymer, "ClZ" is chlorobenzyloxycarbonyl, "Z" is carbobenzoxy, and the remaining abbreviations used are those commonly employed in the practice of peptide chemistry and are well known to those skilled in the art.

REACTION SCHEME I

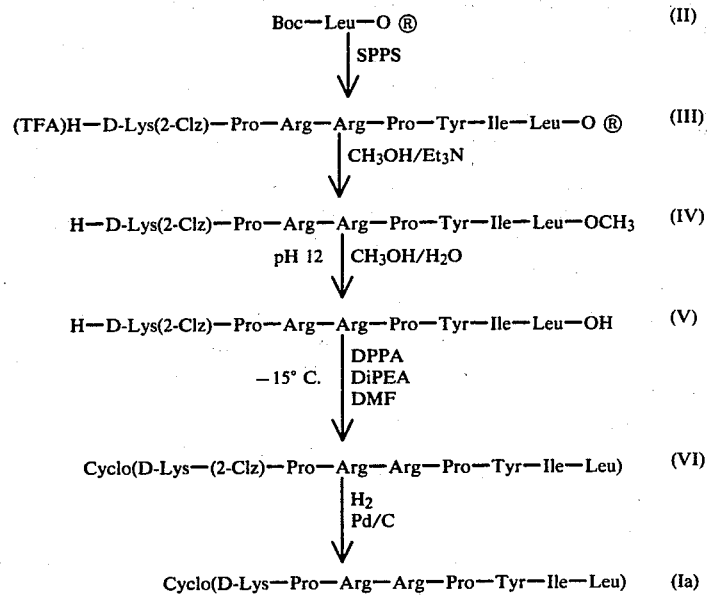

REACTION SCHEME II

REACTION SCHEME II

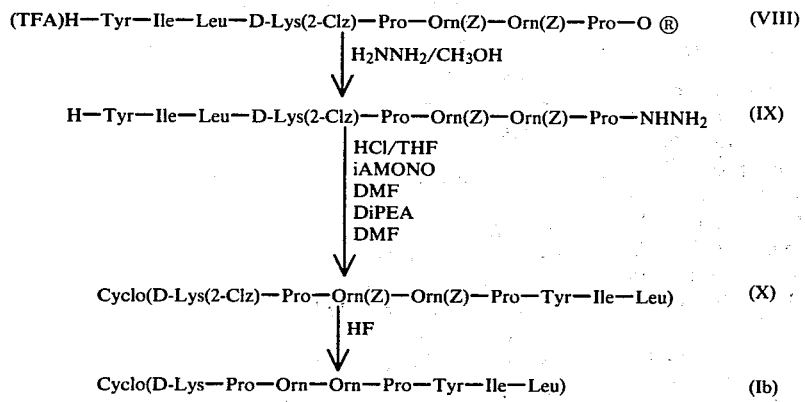

As illustrated in Reaction Scheme I, appropriately blocked peptide or amino acid (II) such as leucine (Leu) blocked with tert-butyloxycarbonyl (Boc) and bound to a resin (O-Ⓡ) is subjected to a standard solid phase peptide synthesis (SPPS), such as those described in the above-identified references which are incorporated herein by reference, to obtain blocked octapeptide (III). Blocked octapeptide (III) is then suspended in a suitable organic solvent such as methanol and triethylamine and stirred at room temperature to afford blocked octapeptide methyl ester (IV).

Blocked octapeptide methyl ester (IV) is saponified in a methanol-water solution adjusted to pH 12 to afford blocked octapeptide acid (V). Treatment of (V) with a mixture of diphenylphosphorylazide (DPPA), diisopropylethylamine (DiPEA), and dimethylformamide (DMF) at −15° C. yields cyclized octapeptide (VI) which is then subjected to catalytic (Pd/C) hydrogenation to remove the blocking groups and provide cyclic octapeptide (Ia).

In Reaction Scheme II, blocked peptide or amino acid (VII) ("Pro"=proline) bound to resin (O-Ⓡ) is elaborated by standard solid phase synthesis (SPPS) to obtain blocked octapeptide (VIII) which is then treated with hydrazine (H₂NNH₂) in a suitable organic solvent such as methanol to afford blocked octapeptide hydrazide (IX). Compound (IX) is then first treated with isoamylnitrite (iAMONO) and hydrogen chloride in tetrahydrofuran (THF) in a suitable organic solvent such as DMF followed by pH ajustment with diPEA in DMF to yield cyclized octapeptide (X). Treatment of cyclized octapeptide (X) with hydrofluoric acid removes the blocking groups and provides cyclic octapeptide (Ib).

The following examples are set forth to further illustrate the cyclic octapeptide analogs of the invention and are intended to be exemplary and not limitative of the invention. Unless otherwise specified, all temperatures are in degrees Celsius.

EXAMPLE 1

Cyclo(D-Lys-Pro-Arg-Arg-Pro-Tyr-Ile-Leu)

Step A:
D-Lys(2-Clz)-Pro-Arg-Arg-Pro-Tyr-Ile-Leu-OCH₃
(TFA) D-Lys(2-Clz)-Pro-Arg(HCl)-Arg(HCl)-Pro-Tyr-Ile-Leu-O Ⓡ, (4.22 g, 2 mmoles) was stirred in 200 ml 10% Et₃N-CH₃OH for 24 hours at room temperature. The resin was separated by filtration and the filtrate was evaporated to dryness in vacuo. The resulting oil was flushed and evaporated to dryness with CH₃OH; yield, 2.3 g. The resin was retreated with 100 ml 10% Et₃N-CH₃OH for 24 hours and separated by filtration. Evaporation of the filtrate followed by flushing of the residue and evaporation to dryness with CH₃OH gave 0.46 g of a second crop.

Step B:
D-Lys(2-Clz)-Pro-Art-Arg-Pro-Tyr-Ile-Leu
The octapeptide ester from Step A, (1.5 g) dissolved in a mixture of 25 ml CH₃OH and 20 ml H₂O, was hydrolyzed at pH 12.2 for 6 hours. The pH of the solution was then adjusted to 5.0 with 1 N HCl and the solvents removed in vacuo. The residual oil was flushed and evaporated to dryness with DMF.

Step C:
Cyclo(D-Lys(2-Clz)-Pro-Arg-Arg-Pro-Tyr-Ile-Leu)
The octapeptide acid from Step B was dissolved in 150 ml of freshly degassed DMF and the pH of the solution adjusted to 7.2 (determined by moistened narrow range pH paper) with N,N-diisopropylethylamine. After cooling to −25° C., 0.7 ml of diphenylphosphorylazide was added. The reaction mixture was stored at −15° C. with periodic pH adjustments for 48 hours. The solvent was then removed in vacuo and the residue partitioned between n-BuOH and H₂O. Evaporation of the organic phase in vacuo left the product as the residual oil.

Step D:
Cyclo(D-Lys-Pro-Arg-Arg-Pro-Tyr-Ile-Leu)
The protected cyclic octapeptide from Step C, dissolved in 35 ml EtOH-5 ml 50% HOAc, was hydrogenated overnight at 45 psi over 500 mg of 10% Pd/C. The catalyst was filtered and the filtrate evaporated to dryness in vacuo. The resulting oil was purified by chromatography on Sephadex G-25SF in 50% HOAc, followed by chromatography on silica gel, eluting with n-BuOH-HOAc-H₂O (3:1:1). The purified product was desalted by gel filtration (Sephadex G-25SF, 2 N HOAc) and then lyophilized; yield, 258 mg. It was characterized by TLC, HPLC, amino acid analysis after acid hydrolysis, and pmr.

EXAMPLE 2

Cyclo-(D-Lys-Pro-Lys-Lys-Pro-Tyr-Ile-Leu
Step A:
D-Lys(2-Clz)-Pro-Lys(2-Clz)-Lys(2-Clz)-Pro-Tyr-Ile-Leu-NHNH₂

A mixture of (TFA)-D-Lys(2-ClZ)-Pro-Lys(2-ClZ)-Lys(2-ClZ)-Pro-Tyr-Ile-Leu-O-Ⓡ (5.04 g, 2 mmols), methanol (50 ml) and anhydrous hydrazine (25 ml) was stirred in a closed vessel for 1.5 hours and filtered. The solid on the filter was washed with methanol (3×50 ml) and the combined filtrates stripped to dryness. Water (75 ml) was added to the residue and the resulting solid filtered and washed with water until the washings gave a negative Tollen's test. The resulting solid was dried under vacuum at 25°, 2.8 g.

Step B:
Cyclo-(D-Lys(2-Clz)-Pro-Lys(2-Clz)-Lys(2-Clz)-Pro-Tyr-Ile-Leu)

The hydrazide from Step A was dissolved in freshly degassed DMF (20 ml) and cooled to −25° under nitrogen. A 5.42 N HCl in THF (1.85 ml, 10 mmol) was added dropwise and allowed to stir 2–3 minutes. Isoamylnitrite (0.3 ml) was added followed by periodic (3–5 minutes) additions of 0.02 ml isoamylnitrite until a faint positive starch-potassium iodide test was obtained. The solution was diluted into 200 ml of degassed DMF at −35° and the pH of the solution adjusted to 7.2–7.6 with diisopropylethylamine. The reaction mixture was then stored at −20° with periodic pH adjustments for seven days. The DMF was removed in vacuo and the residue stirred with water, filtered and dried, 2.40 g.

Step C:
Cyclo-(D-Lys-Pro-Lys-Lys-Pro-Tyr-Ile-Leu)

The protected cyclic peptide from Step B was added to anisole (3 ml) and treated with anhydrous liquid HF (25 ml) at 0° for 1 hour. After removal of the HF, the residue was stirred with ether, filtered, washed well with ether and dried. Gel filtration (50% HOAc, Sephadex G-25SF) followed by lyophilization gave 0.217 g of the desired product (HPLC, >98% pure, Spinco analysis satisfactory).

EXAMPLE 3

Cyclo-(D-Lys-Pro-Orn-Orn-Pro-Tyr-Ile-Leu)

Following the procedure of Example 2, the titled cyclic octapeptide was obtained using ornithine in place of lysine.

EXAMPLE 4

Cyclo(D-Lys-Pro-Orn-Orn-Pro-Trp-Ile-Leu)

Using the appropriate starting materials, cyclo(D-Lys(2-Clz)Pro-Orn(Z)-Orn(Z)-Pro-Trp-Ile-Leu) was prepared by the procedures described in Example 2, Steps A and B, from approximately 2 mmoles of the resin-bound protected linear peptide. This protected cyclic peptide, dissolved in a mixture of 75 ml ethanol, 10 ml HOAc, and 10 ml H$_2$O, was hydrogenated overnight at 40 psi over 400 mg of 20% Pd(OH)$_2$/C. After a probe on TLC indicated incomplete hydrogenolysis, 400 mg of fresh catalyst was added and the hydrogenolysis at 40 psi was continued for an overnight period. The catalyst was then filtered and the filtrate evaporated to dryness in vacuo. The residual oil was purified by two successive gel filtration through Sephadex G-25SF ((1) 50% HOAc; (2) 2 N HOAc). The purified, lyophilized product (150 mg) was characterized by TLC, HPLC, amino acid analysis after acid hydrolysis, and pmr.

What is claimed is:

1. A cyclic octapeptide having the formula

Cyclo(D-Lys-Pro-B-B-Pro-C-Ile-Leu)     (I)

wherein:
B is a basic amino acid residue selected from the group consisting of 2,4-diamino butyric acid, lysine, arginine, ornithine, and homoarginine; and
C is tyrosine, or tryptophane.

2. The octapeptide of claim 1 wherein B is lysine or ornithine; and, C is tyrosine.

3. The cyclic octapeptide:
Cyclo(D-Lys-Pro-Arg-Arg-Pro-Tyr-Ile-Leu).

4. The cyclic octapeptide:
Cyclo(D-Lys-Pro-Orn-Orn-Pro-Tyr-Lle-Leu).

5. The cyclic octapeptide:
Cyclo(D-Lys-Pro-Lys-Lys-Pro-Tyr-Ile-Leu).

6. The cyclic octapeptide:
Cyclo(D-Lys-Pro-Orn-Orn-Pro-Trp-Ile-Leu).

* * * * *